United States Patent [19]
Zadno-Azizi et al.

[11] Patent Number: 6,156,054
[45] Date of Patent: *Dec. 5, 2000

[54] MEDICAL WIRE INTRODUCER AND BALLOON PROTECTIVE SHEATH

[75] Inventors: G. Reza Zadno-Azizi, Newark; Mukund Patel, San Jose; Andres D. Tomas, Union City; Hung Ha, San Jose; Celso Bagaoisan, Union City, all of Calif.

[73] Assignee: Percusurge, Inc., Sunnyvale, Calif.

[ * ] Notice: This patent is subject to a terminal disclaimer.

[21] Appl. No.: 09/368,397

[22] Filed: Aug. 4, 1999

Related U.S. Application Data

[63] Continuation of application No. 09/047,303, Mar. 24, 1998, Pat. No. 5,997,562, which is a continuation of application No. 08/874,307, Jun. 13, 1997, abandoned.

[51] Int. Cl.[7] ................................................. A61M 29/00
[52] U.S. Cl. ........................ 606/194; 606/108; 606/180; 604/158
[58] Field of Search .................................. 606/108, 194, 606/180, 184; 604/171, 158, 264, 280

[56] References Cited

U.S. PATENT DOCUMENTS

| | | | |
|---|---|---|---|
| 4,723,550 | 2/1988 | Bales et al. | 606/108 |
| 4,726,374 | 2/1988 | Bales et al. | 606/108 |
| 5,318,532 | 6/1994 | Frassica | 606/194 |
| 5,324,306 | 6/1994 | Makower et al. | 606/108 |
| 5,397,305 | 3/1995 | Kawula et al. | 604/96 |
| 5,439,447 | 8/1995 | Miraki | 604/96 |
| 5,505,725 | 4/1996 | Samson | 606/108 |
| 5,603,698 | 2/1997 | Roberts et al. | 606/108 |
| 5,997,562 | 12/1999 | Zadno-Azizi et al. | 606/194 |

Primary Examiner—Pedro Philogene
Attorney, Agent, or Firm—Knobbe, Martens, Olson & Bear LLP

[57] ABSTRACT

The present invention provides a protective sheath assembly which combines the function of an introducer, the function of a protective sheath and the function of a sealing valve in an integrated assembly. The protective sheath assembly of the present invention preferably comprises a protective sheath, a strain-relief tubing, and a connecting member or a hub. These parts are mounted, removably or permanently, into an integral device. The protective sheath assembly can also be used in combination with an introducer such as a needle introducer. The protective sheath has a proximal end, a distal end, and an elongated hollow body defining a lumen along the longitudinal direction of the protective sheath. A hub is provided to secure the proximal end of the protective sheath to an introducer. The lumen of the protective sheath serves to accommodate and protect a balloon catheter, as well as seal around the catheter.

12 Claims, 4 Drawing Sheets

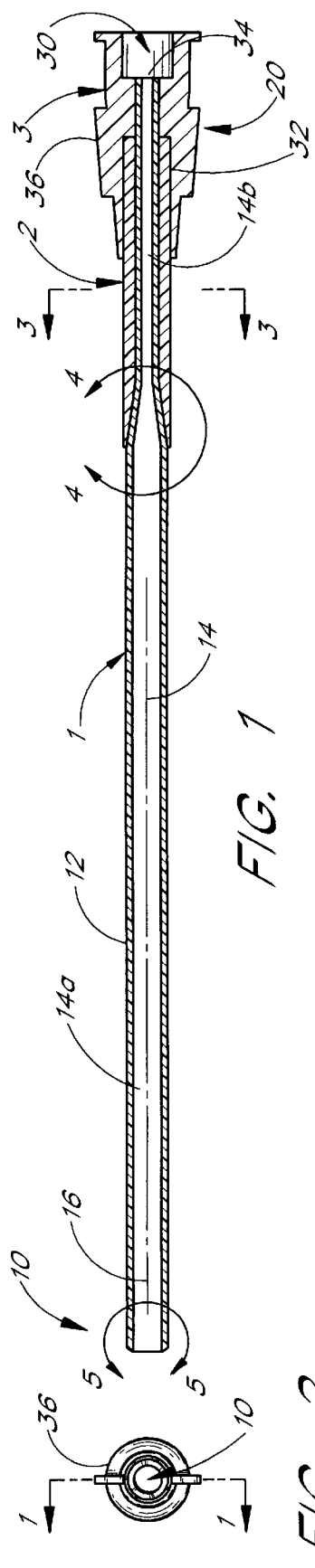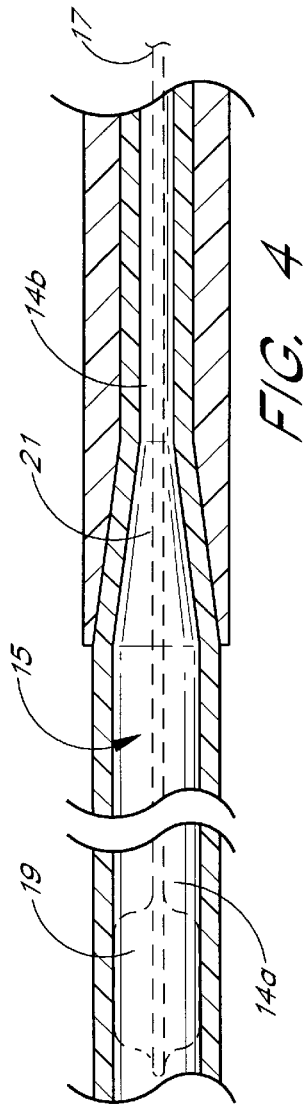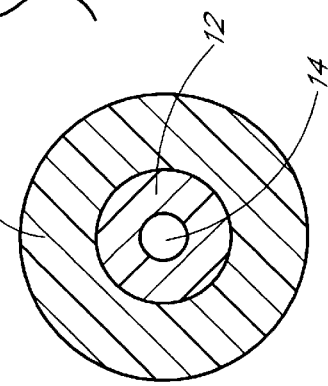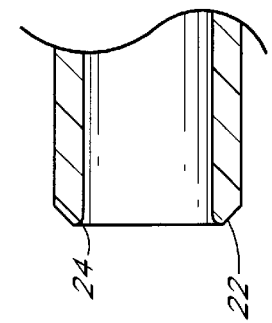

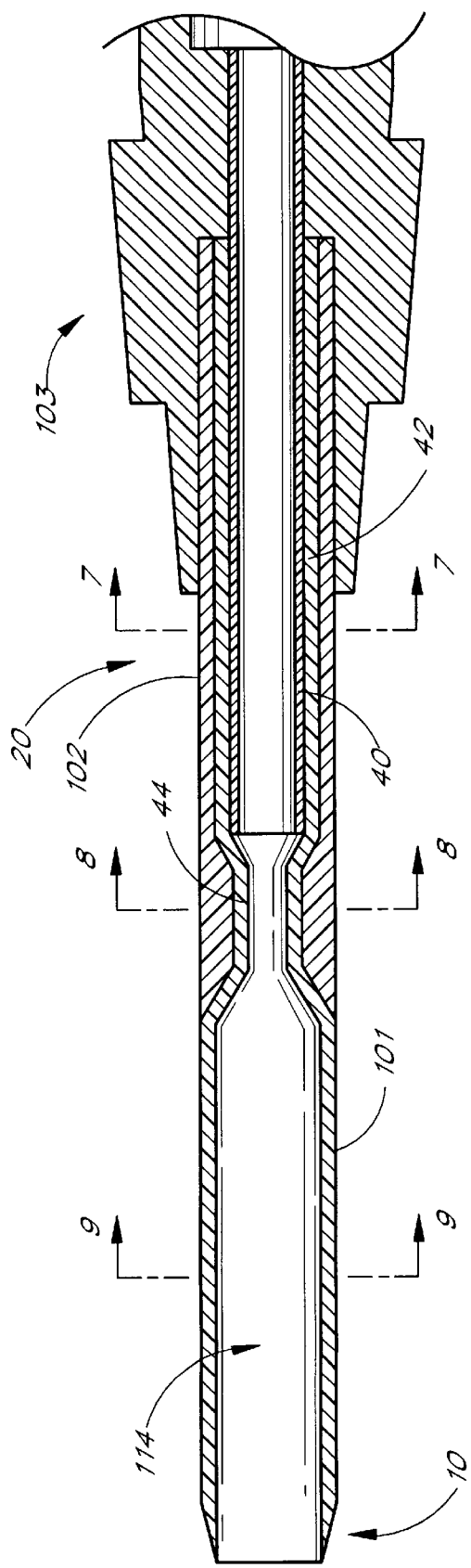
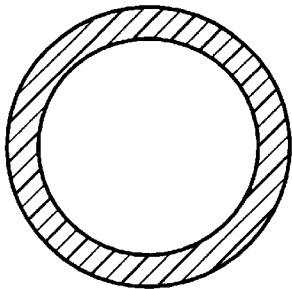
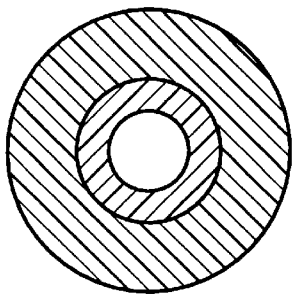
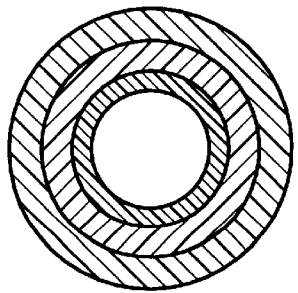

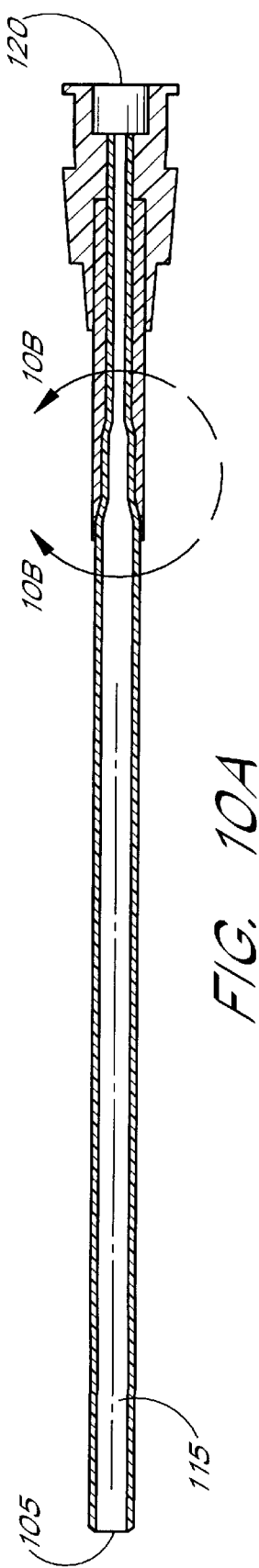
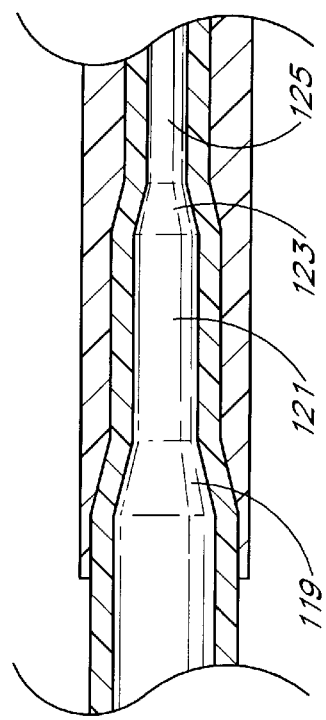
FIG. 10A
FIG. 10B

MEDICAL WIRE INTRODUCER AND BALLOON PROTECTIVE SHEATH

CROSS-REFERENCE TO RELATED APPLICATIONS

This application is continuation of U.S. patent application Ser. No. 09/047,303, filed Mar. 24, 1998, now U.S. Pat. No. 5,997,562, which is a continuation of U.S. patent application Ser. No. 08/874,307, filed Jun. 13, 1997, abandoned.

BACKGROUND OF THE INVENTION

1. Field of Invention

The present invention relates to a medical wire introducer, and more particularly, to a protective sheath assembly for introducing a wide variety of balloon catheters into blood vessels. The present invention also relates to a wire introducer/protective sheath assembly and methods of constructing and using same.

2. Description of Related Art

Minimally invasive surgical techniques, including intravascular techniques such as angioplasty, have had a rapid development and wide acceptance within the medical fields. In these surgical procedures, usually a percutaneous or arterial sheath is introduced through a puncture or an incision in the patient's skin to provide percutaneous access to blood vessels. This step is followed by insertion of a catheter through the arterial sheath and its advancement through the arteries to target sites. The catheter can be equipped with different devices at its distal end, such as a balloon. These devices can serve a variety of functions, such as occluding the vessel so as to block blood flow, and dilating occluded blood vessels during angioplasty. Solid or hollow thin wires, called guidewires, are commonly used to guide the insertion of catheters.

Angioplasty balloon catheters can be roughly divided into three categories: over-the-wire (OTW) systems, single-operator-exchange (SOE) or monorail systems, and fixed-wire systems (also called "balloon-on-a-wire"). In an OTW system, a solid guidewire is used to guide a balloon catheter, which is tracked coaxially over the guidewire and can be moved relative to it. SOE balloon catheters are modified OTW catheters, i.e., only the distal portion of a SOE balloon catheter tracks coaxially over the guidewire. In a fixed-wire system, a hollow guidewire is in fluid communication with a balloon mounted at its distal end to supply inflation fluid to the balloon. The guidewire typically has a soft tip at its distal end to guide the placement in the vessel.

Vascular access may include a femoral approach, a brachial approach or a radial approach. A commonly adopted procedure for intravascular surgery through a femoral approach typically involves the following steps: (a) identifying the femoral artery and administrating local anesthetic to the patient; (b) inserting a needle into the femoral artery (or an appropriate peripheral blood vessel) and waiting for blood to flow out through the needle; (c) introducing a guidewire into the blood vessel through the needle and then removing the needle leaving the guidewire in place within the blood vessel; (d) tracking an arterial (percutaneous) sheath and dilator over the guidewire into the blood vessel, so that the distal end of the arterial sheath enters the vessel; (e) removing the dilator and the guidewire leaving the arterial sheath in place; (f) introducing a guide catheter over a guidewire through the percutaneous sheath and advancing it around the aortic arch; (g) removing the guidewire; (h) connecting the guide catheter to an inflation device and a steering tool through a Y-adaptor and/or to a manifold assembly through another Y-adaptor, with the manifold assembly usually being connected to a pressure transducer and a syringe; (i) introducing a catheter over a guidewire through the guide catheter and the Y-adaptor, and advancing it through the arteries until the distal end of the catheter reaches the treatment site. Alternatively, if a "balloon-on-wire" catheter, such as a distal occlusion wire (DOW), is being used in the last step the catheter may be directly inserted into the blood vessel through the guide catheter and Y-adaptor.

Obviously, during this process, blood may bleed back under arterial pressure. In order to avoid excess bleeding and possible air embolisms, a hemostasis valve or a Touhy-Borst valve is usually installed in the Y-adaptor. Various hemostasis valves have been developed. A hemostasis valve is typically composed of one or more resilient, cylindrical pieces having slits or holes therethrough. These slits and/or holes are sized and configured so that they are normally closed, but may permit a guidewire or a catheter to be forced through while maintaining a seal around the guidewire or catheter.

However, when a fixed-wire catheter, such as a DOW, is used, it becomes very difficult to insert the catheter through a hemostasis valve because the distal end of a "balloon-on-wire" catheter usually has a soft tip to guide the catheter while preventing damage to the blood vessel. A concomitant problem of having a balloon with a soft tip, however, is that the soft tip is capable of being damaged while inserting it through the hemostasis valve. Thus, there is a further need for a protective sheath to shield the balloon and the soft tip when introducing the same through a hemostasis valve.

Presently, either a guidewire needle introducer or a protective sheath, are separately used to introduce a balloon catheter into a guide catheter via a hemostasis valve mounted within the Y-adaptor. However, when using either procedure, the problem of back blood flow still exists as the hollow protective sheath, or the large needle, is inserted into the Y-adaptor. For some catheter devices of the balloon-on-wire type, such as a DOW, these methods, i.e. using either a protective sheath or a large needle introducer, also will be very cumbersome, time consuming, and cause greater back bleed. Thus, there exists an urgent need for an introducer device which can be conveniently and safely utilized to insert a balloon catheter or any-fixed wire devices during intravascular surgery.

SUMMARY OF THE INVENTION

The present invention provides a protective sheath assembly for introducing a fixed-wire balloon catheter into a blood vessel through a hemostasis valve or a Touhy-Borst valve. Another aspect of the present invention is to provide a wire introducer/protective sheath assembly and methods of constructing and using same.

The protective sheath assembly of the present invention combines the function of an introducer with both the function of a protective sheath and the function of a sealing valve, thus forming an integrated protective sheath assembly. The protective sheath assembly of the present invention comprises a protective sheath having a proximal end, a distal end, and an elongated hollow body defining a lumen along the longitudinal axis of the protective sheath. The lumen of the protective sheath further comprises three portions: a proximal portion, a distal portion, and a transitional portion between the two. The inner diameter of the distal portion is larger than the diameter of the balloon, and the inner diameter of the proximal portion is larger than the outer diameter of the guidewire. The lumen of the protective sheath serves several functions. These include: protecting the balloon and the soft tip, accommodating movement of the guidewire, and forming a seal around it.

In one embodiment, the dimension of the lumen of the protective sheath is designed so that the inner diameter of the lumen at its proximal portion is slightly larger than the outer diameter of the guidewire, thus providing adequate and smooth passage of the guidewire. The clearance between the two diameters, or between the inner surface of the proximal portion of the protective sheath and the outer surface of the guidewire, should be small enough so as to substantially minimize back blood flow under arterial pressure. In addition, other sealing mechanisms can be used in the proximal portion. For example, an O-ring or a sealing sleeve can be installed within the proximal portion of the protective sheath through a connecting member or by alternative means. In this case, the protective sheath body and the lumen may have uniform inner and outer diameters. It is also possible to use a reducing member to connect the proximal portion with a smaller dimension to the distal portion with a larger dimension.

At the distal portion of the protective sheath, a larger dimension of the lumen is preferably provided to accommodate and protect the balloon and the flexible tip mounted on distal end of a guidewire. The protective sheath preferably has a flared inner surface and a tapered outer surface at its distal end, thereby permitting easier back load of the guidewire and insertion of the protective sheath through a hemostasis valve to a blood vessel. Overall, a smooth transition of the lumen dimension between the proximal portion is desirable. The smooth loading of the guidewire is facilitated by the relative dimensions of the distal and proximal portions, with the proximal portion usually having a smaller diameter and the distal portion usually having a larger diameter. The longitudinal center line of the lumen of the protective sheath usually is configured as a straight line, but may also be made curved at a desired angle.

In another embodiment, an elongated tubular sleeve is used to enclose the proximal portion of the protective sheath in order to further support and hold the sheath. In this case, the sleeve has an inner diameter slightly larger than the outer diameter of the proximal portion of the protective sheath thereby substantially covering the entire proximal portion at the point where the protective sheath has a smaller outer diameter. The proximal end of the protective sheath and the tubular sleeve is connected to a hub or a connecting member.

In another embodiment, a metal hypotube or a needle is partially inserted into the lumen of the protective sheath from the proximal end to facilitate the smooth movement of the guidewire. The metal hypotube has an inner diameter slightly larger than the outer diameter of the guidewire so that the guidewire can be freely moved through the metal hypotube. The outer diameter of the metal hypotube is slightly larger than the inner diameter of the lumen at the proximal portion of the protective sheath.

The cross-sectional area of the protective sheath is preferably circular, but other shapes, such as an oval shape, are possible. More than one channel can be provided in the protective sheath. The cross-sectional plane at the distal end of the protective sheath assembly also does not have to be perpendicular to the longitudinal axis, and may be of a different shape.

A connecting member or a hub is provided at the proximal end of the protective sheath. The connecting member has a distal side with a first mechanism for receiving the proximal end of the protective sheath and a proximal side with a second mechanism for optionally receiving an introducer.

The protective sheath of the present invention can be used alone or in combination with an introducer, such as a needle introducer. The introducer which is used with the protective sheath of the present invention has a first end proximal to the operator, a second end for connecting to the protective sheath, and an elongated body defining a cavity along its longitudinal axis for receiving a guidewire. The connection between the introducer and the protective sheath can be made in different ways. In one embodiment, the connecting member is a female luer lock having a proximal end with a cup-shaped cavity for receiving the second end of the introducer, a distal end with an elongated cavity for receiving the proximal end of the protective sheath, and a through-hole aligned with the lumen of the protective sheath and the longitudinal cavity of the introducer. The proximal end of the protective sheath is inserted into the distal end of the female luer lock through the elongated cavity. The second end of the introducer is inserted into the proximal end of the female luer lock through the cup-shaped cavity. It is desirable to make those connections removable by slip-fitting, if necessary a glue can be used. It is also apparent that other locking structures can be used, for example, a ridge-grooved connection.

One aspect of the present invention includes a protective sheath assembly for introducing a balloon catheter containing a balloon and a soft tip into the blood vessel of a patient. This protective sheath has a proximal end, a distal end, and an elongated body defining a lumen along a longitudinal axis of the protective sheath. The lumen also has a proximal portion and a distal portion and is constructed so that the catheter can be moved through the lumen. An embodiment of the protective sheath assembly includes a balloon catheter capable of being moved through the lumen, while maintaining a seal against blood bleed. This seal is maintained by the proximal portion of the lumen containing the balloon and the soft tip.

Another embodiment of the present invention also includes a protective sheath assembly containing a strain-relief tubing enclosing the proximal portion of the protective sheath. The protective sheath assembly may also contain a hub which is connected to the proximal end of the protective sheath. The distal end of the protective sheath assembly may contain a flared inner surface. The protective sheath assembly also includes a transition point between the narrower proximal portion and the broader distal end of the protective sheath that is smoothly tapered.

According to another aspect of the present invention, a protective sheath assembly for introducing a balloon catheter also contains a metallic hypotube having a diameter slightly larger than the diameter of the balloon catheter. This hypotube is inserted into the proximal portion of the protective sheath with part of the proximal portion not touching the hypotube. This configuration facilitates the balloon catheter being moved through the lumen and the hypotube, while maintaining a seal against blood bleed, or back blood flow. An embodiment of this protective sheath assembly, includes a hypotube with an inner diameter that is larger than the inner diameter of the part of the proximal portion of the protective sheath which is not touching the metallic hypotube. Another embodiment of this protective sheath, containing a hypotube, includes a hub connected to the proximal end of the protective sheath.

Still another aspect of the present invention includes an introducer contained within the protective sheath assembly, which facilitates the introduction of the catheter containing a balloon and a soft tip into a blood vessel system. This protective sheath assembly is configured to have a proximal end, a distal end with a flared inner surface and tapered outer surface, and an elongated hollow body defining a lumen along the longitudinal axis of the sheath, with the lumen having a proximal portion and a distal portion, and the proximal portion having an inner diameter smaller than that of the distal portion, and slightly larger than the outer diameter of the catheter. The introducer has a first end, a second end, and an elongated body defining a cavity along its longitudinal axis. It also contains a connecting member for securing the protective sheath to the introducer. This connecting member has a distal end with a first mechanism for receiving the proximal end of the protective sheath, a proximal end with a second mechanism for receiving the introducer, and a hole along the center line of the connecting member.

Another aspect of the present invention includes a method for making a protective sheath assembly having an introducer, a protective sheath, and a connecting member. This method comprises the steps of extruding a plastic tubing of desired dimension; inserting a mandrel of predetermined dimension into the plastic tubing; exposing a portion of the plastic tubing to a hot air; heating and stretching the exposed end of the plastic tubing to a predetermined smaller diameter; flaring the other end of the tubing; inserting the stretched end into a strain-relief tubing; and finally, connecting the stretched end and the strain-relief tubing to one side of a connecting member. An embodiment of this method of making a protective sheath assembly/introducer includes extruding a plastic tubing containing one or more stepped regions where the regions consist of variable diameters.

According to another aspect of the present invention, a method of using a protective sheath assembly in angioplasty would include the steps of: inserting a guide catheter into a blood vessel of a patient; connecting a Y-adaptor containing a hemostasis value to the guide catheter; inserting a balloon catheter into the protective sheath assembly having a proximal end and a distal end; inserting the distal end of the protective sheath assembly into the Y-adaptor through the hemostasis valve; and advancing the balloon catheter towards a treatment site. This method of using the protective sheath assembly in angioplasty also may include placing an arterial protective sheath between the guide catheter and the Y-adaptor. While utilizing this method of using the protective sheath assembly, it is possible to remove the protective sheath either before of after the catheter is advanced towards the treatment site.

The general requirements for a protective sheath or an introducer include: (1) it should have high lubricity and (2) produce minimum or no back flow of blood. Additionally, the introducer could be made peelable, that is, it would be able to move a balloon-tipped guidewire in and out without resistance while a clamp is in position. The introducer assembly of the present invention fulfills these two requirements and provides other advantages. It protects the tip-end of the balloon of a guidewire and prevents excess back blood flow while introducing the guidewire through a hemostasis valve. Moreover, the flared distal end of the protective sheath makes it very convenient to back load a guidewire. Finally, the protective sheath of the present invention is very easy to operate and significantly reduces loading time due to its single-component design.

BRIEF DESCRIPTION OF THE DRAWINGS

FIG. 1 is a side cross-sectional view of the protective sheath assembly according to one embodiment of the present invention;

FIG. 2 is a perpendicular cross-sectional view of the protective sheath assembly of 1.

FIG. 3 is a perpendicular cross-sectional view of the protective sheath assembly of FIG. 1 as seen through sectional line 3—3.

FIG. 4 is an enlargement of the transition section of the protective sheath assembly of FIG. 1 as indicated by line 4—4.

FIG. 5 is an enlargement of the distal end of the protective sheath assembly of FIG. 1 as indicated by line 5—5.

FIG. 6 is a side, partial cross-sectional view of the protective sheath assembly according to another embodiment of the present invention.

FIG. 7 is a perpendicular cross-sectional view of the protective sheath assembly of FIG. 6 as seen through sectional line 7—7.

FIG. 8 is a perpendicular cross-sectional view of the protective sheath assembly of FIG. 6 as seen through sectional line 8—8.

FIG. 9 is a perpendicular cross-sectional view of the protective sheath assembly of FIG. 6 as seen through sectional line 9—9.

FIG. 10 is a side cross-sectional view of the protective sheath assembly of the present invention according to another embodiment having multiple internal lumen diameters.

DETAILED DESCRIPTION OF THE PREFERRED EMBODIMENTS

Figure 11:
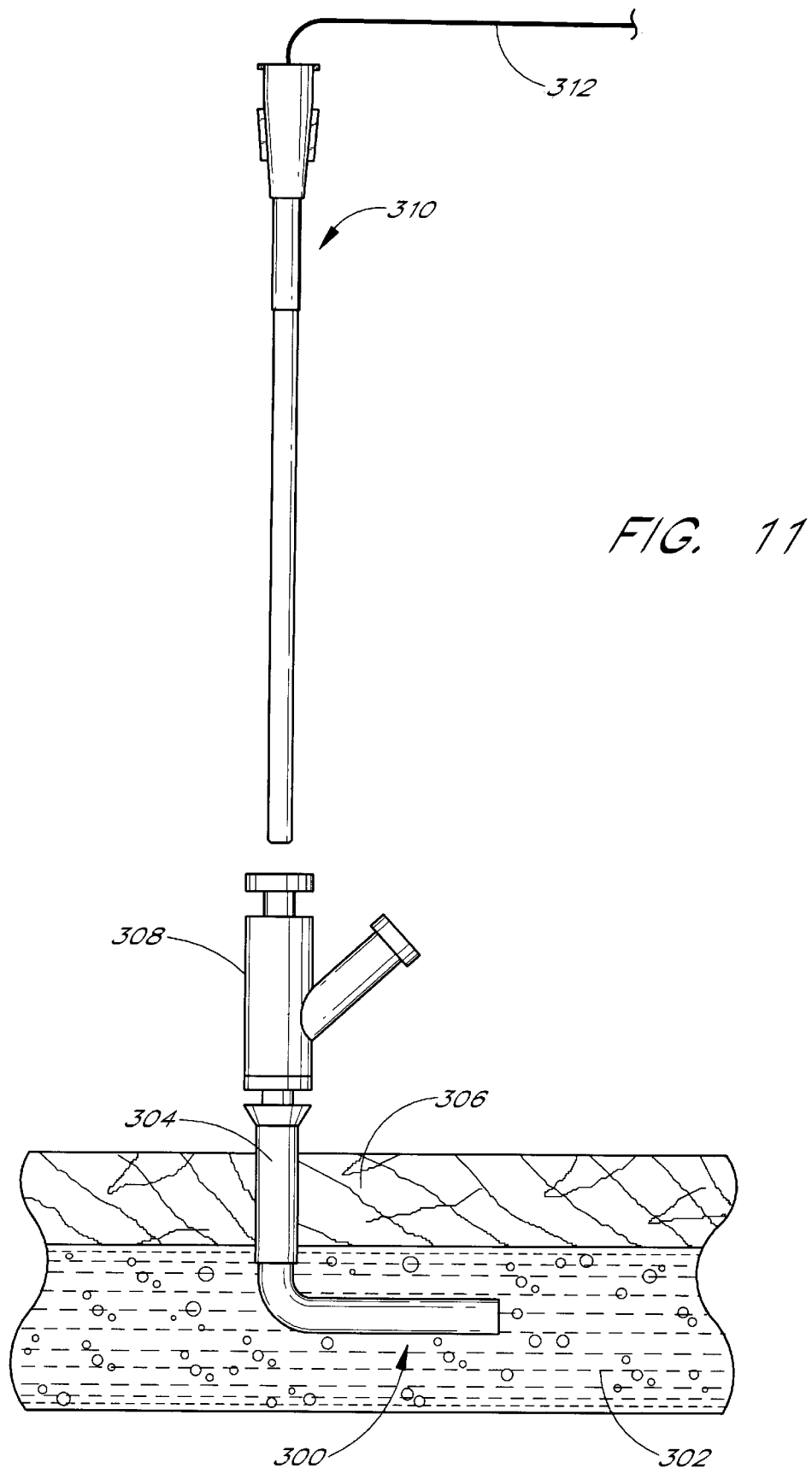
FIG. 11 is a schematic representation of a surgery system using the protective sheath assembly of the present invention to introduce a catheter with balloon into a blood vessel.

FIG. 1 shows the protective sheath assembly according to one embodiment of the present invention. As illustrated in FIG. 1, the protective sheath assembly has three major parts: a protective sheath 1, a female luer lock 3, and a strain-relief tubing 2. The protective sheath 1 has an elongated tubular body 12 defining an elongated lumen 14 along a longitudinal axis 16. FIG. 2 is an end view of the sheath 1 of FIG. 1 looking from the distal end 10 toward the proximal end 20, wherein is located the plane 36 to facilitate the handling of the sheath 1. FIG. 3 is a cross-sectional view taken through the proximal end 20 of the sheath 1 and illustrating a strain relief tubing 2 as positioned about the elongated tubular body 12 which defines the lumen 14.

The protective sheath 1, shown in FIG. 1, also has a distal end 10 and a proximal end 20. As shown in FIG. 5, the distal end 10 contains a tapered outer diameter 22 and a flared inner diameter 24. This outer taper 22 configuration facilitates introduction of the sheath 1 into the Touhy adapter, while the inner flare 24 provides easier introduction of the wire 17 into the sheath.

The lumen 14 can be further divided into two portions, the proximal portion 14b with a smaller dimension starting from the proximal end 20 and the distal portion 14a with the longer dimension starting from the distal end 5—5 and extending over a relatively large part of the protective sheath 1. Of course, the proximal end could also be made longer if desired.

The dimension of lumen 14 at the proximal portion 14b may vary depending on the outer diameter of the guidewire to be used. The inner diameter and the length of the proximal portion 14b of lumen 14 is designed so that the guidewire can be moved smoothly through the lumen 14, while providing a good seal between the guidewire and the lumen 14 so as to prevent, or minimize, back blood flow under arterial pressure. The dimension of the distal portion 14a of lumen 14, including the length and the inner diameter, may vary depending on the sizes of the balloon and the soft tip. However, the distal portion of 14a should be large enough to accommodate and protect the balloon, as well as the soft tip of a balloon catheter, or other fixed wire devices.

It will be noted that various configurations and dimensions are possible with respect to the proximal portion 14b in order to accommodate the balloon or other medical device intended for use in connection with the present protective sheath assembly. Furthermore, the combination of a larger diameter distal section and a smaller diameter proximal section may be reversed, depending upon the configuration of the catheter or other medical device to be protected by the sheath assembly. Thus, as discussed below in more detail in connection with FIGS. 6, 10A and 10B, other combinations of lumen configurations are within the scope of the present invention. However, one preferred application of the present sheath assembly is illustrated in FIG. 4. FIG. 4 illustrates a broken side cross-sectional view of the sheath assembly of FIG. 1 and further illustrates in dotted lines a catheter 15 positioned within the lumen 14 of the protective sheath 1. Specifically, the catheter 15 comprises a guidewire 17 extending from the proximal end 20 of the sheath 1 and toward the distal end 10. Mounted on the distal end of the guidewire 17 is a medical balloon 19 which is housed protectively within the distal portion 14a of the sheath 1. It will be noted that the guidewire 17 is housed snugly in the proximal portion 14b of the lumen of the sheath in order to prevent or at least minimize back blood flow under arterial pressure. It will be noted that the longitudinal position of the balloon is not particularly important so long as it is protectively contained within the lumen 14a. In a method of the present invention, the proximal end of the guidewire 17 is loaded into the sheath 1 beginning at the distal end 10. This loading is facilitated by a transition section 21, as illustrated in FIG. 4, located between the distal section 14a and the proximal section 14b of the lumen 14. This lumen transition 21 between the proximal portion 14a and the distal portion 14b should be smooth to assist the loading of a balloon guidewire. Although, as noted above, the present chief assembly can be utilized with a wide variety of medical devices, one fixed wire catheter which is suitable for use therewith is illustrated and described in detail in copending application Ser. No. 08/812,876, filed Mar. 6, 1997, entitled "Hollow Medical Wires and Methods of Constructing Same", which is hereby incorporated by reference in its entirety.

Referring again to FIG. 1, the female luer lock 3 has a cup-shaped cavity 30 at its proximal side, a cylindrical cavity 32 at its distal side, a through-hole 34 in the center along its longitudinal axis, and a wing 36. The strain-relief tubing 2 has an inner diameter substantially the same as, or slightly larger than the outer diameter of the proximal portion of the lumen 14 and forms a tight fit with the protective sheath 1. At the distal end of the strain-relief tubing 2, its inner surface is flared to fit the outer surface of the protective sheath 1 as shown in FIG. 4. The outer diameter of the strain-relief tubing matches with the inner diameter of the cylindrical cavity 32 so that they can be connected by slip-fit. The insertion of the proximal portion of the lumen 14 into the strain-relief tubing 2 is also accomplished by slip-fitting. The cup-shaped cavity 30 serves to optionally receive a needle introducer (not shown), or flushing devices.

The protective sheath assembly of the present invention is not limited to a specific dimension. The particular protective sheath assembly, shown as an example in FIG. 1, has the following dimensions: the total length of the protective sheath 1 is about 3.6 in. with the proximal portion about 1 in., the distal portion about 2.5 in., and the transition between these two portions about 0.1 in. The inner diameter of the proximal portion is about 0.017 in., the inner diameter of the distal portion is about 0.05 to 0.075 in. The length of the strain-relief tubing 2 is about 1 in.

In FIG. 6, another embodiment is shown. The protective sheath assembly has a protective sheath 101, a strain-relief tubing 102, and a female luer lock 103 similar to those discussed above in FIG. 1. However, in this embodiment a metallic hypotube (or a needle) 40 is inserted into the proximal end 20 of the protective sheath 101. The outer diameter of the metallic hypotube is slightly larger than the original inner diameter of the proximal portion of the lumen 114. The metallic hypotube is inserted into the smaller diameter of the lumen 114, preferably by heating the protective sheath to a temperature high enough to soften it. The metallic hypotube is forced into the proximal portion of the lumen 114, followed by cooling and subsequent hardening of the protective sheath. By this heating and cooling process, the hypotube 40 is firmly held within the proximal portion 20 of the protective sheath 101. If necessary, the heating and cooling process can be conducted after the strain-relief 102 tubing has been inserted onto the proximal portion 20 of the protective sheath 101. The insertion of the hypotube 40 divides the proximal portion of the protective sheath 101 into two parts: a first part 42 encloses the hypotube 40, and a second part 44 which is not in contact with the metallic hypotube 40. As shown in FIG. 6, the inner diameter of the proximal portion second part 44, which is defined by the original inner diameter of the proximal portion of the protective sheath 101, is smaller than the inner diameter of the hypotube 40. A larger inner diameter of the hypotube 40 facilitates smooth movement of a guidewire, while the second part 44 provides a good seal around the guidewire. Thus, by adjusting the relative length of the hypotube 40 and the second part 44 one may balance the requirements of attaining smooth guidewire movement as well as a good seal around the guidewire. The distal end of the protective sheath 101 may have a flared inner diameter and a tapered outer diameter, as illustrated in the embodiment of FIG. 1.

The protective sheath, the strain-relief tubing, and the hub may be molded into a single piece. Although the protective sheath assembly of FIG. 6 is not limited to any specific dimension, this embodiment has the following dimensions: the protective sheath 101 has total length about 10–12.5 cm with the first part 42 about 3–4 cm, the second part 44 about 1–1.5 cm (including the smooth transition part) and the distal portion about 6–7 cm. The inner and outer diameter of the distal portion of the protective sheath 101 are 0.05 to 0.075 in. and 0.08 to 0.10 in., respectively. The inner diameter of the second part 44 is about 0.017 in. The inner and outer diameter of the metallic hypotube 40 are about 0.02 and 0.035 in., respectively. The strain-relief tubing 102 has a length about 4–5.5 cm.

The protective sheath, the female luer lock, and the strain-relief tubing of the present invention can be made from various polymer materials such as PEBAX, PE, PEEK, FEP, PTFE, polyimide (Nylon), polycarbonate, etc. The female luer lock or connecting member can also be made of metals such as stainless steel.

There are various ways to mount different parts of the protective sheath assembly according to the present invention. For example, the strain-relief tubing and the protective sheath can be glued together, or produced as a single unit, or as shrink tubing (which is shrunk). The strain-relief tubing can be mounted to the female luer lock through a ridge-grooved mechanism. The female luer lock can be replaced with other connecting devices. These variations would be obvious to one skilled in the art and are considered within the scope and spirit of the present invention.

Yet another embodiment of the sheath assembly of the present invention is shown in FIGS. 10A and 10B. This embodiment, may be constructed at its proximal end 120 in a manner similar to either of the embodiments of FIG. 1 or 6, the distal end of the sheath 105, on the other hand, is provided with multiple cross-sectional diameters. Thus, in this embodiment, a larger diameter section is shown at the distal end of the sheath with a conical or frusto-conical transition section 119 causing a lumen 115 to transition down to a smaller diameter section 121. This smaller section in turn is further reduced down through another conical section 123 to form the smallest diameter 125, which passes through the proximal end to provide a sealing portion around the guidewire. The sheath of this embodiment helps to accommodate catheters having similar transitions in diameter, or it can accommodate different balloon sizes.

Construction And Use

In addition to the methods of construction discussed above in connection with FIG. 6, the present invention also provides a method for making the protective sheath and for making the protective sheath assembly. The protective sheath can be made by necking down a polymer tubing of an appropriate size, bonding a strain-relief tubing or sleeve over the proximal portion of the protective sheath, flaring the inner surface, tapering the outer surface at the distal end of the protective sheath, and attaching a hub or connecting member to the proximal end of the protective sheath. The sheath can also be made from a variable diameter extruded plastic without the need for necking.

In one embodiment, the method for making the protective sheath comprises the following steps: (1) extruding a plastic tubing such as a PE tubing of desired diameter and length; (2) inserting a mandrel of desired outer diameter into the plastic tubing; (3) exposing 1.5–2 in. of the plastic tubing at one end in a hot air box and covering the remaining portion of the plastic tubing with a PTEE sleeve; (4) heating and stretching the exposed end of the plastic tubing in the hot air box; (5) flaring the necked end by inserting a tapered pin at an appropriate temperature in the air box and trimming the ends. Also, it is apparent that various modifications can be made in the above discussed process. Once the protective sheath is made, it can be easily assembled with a connecting member and a strain-relief tubing, or with an introducer. It is also possible to extrude a tube with variable diameter.

Method of Use

Referring FIG. 11, in using the protective sheath assembly or the introducer/protective sheath assembly of the present invention, first a guide catheter is inserted into the blood vessel according to the procedure described in the background section, and incorporated herein. As shown in FIG. 11, the guide catheter 300 is inserted into a blood vessel 302 through an optional arterial sheath 304. The arterial sheath 304 is inserted into the blood vessel through the skin 306 according to steps (a)–(c) described in the background section. A Y-adaptor 308 is connected to the proximal end of the guiding catheter 300. A hemostasis valve or a Touhy-Borst valve is installed inside the Y-adaptor to prevent blood flow. A DOW (or other fixed-wire catheter) 312 is inserted into the protective sheath assembly 310 of the present invention by introducing the proximal end of the DOW 312 (the end without a balloon) into the distal end of the protective sheath assembly 310 and advancing it until the balloon and the soft tip at the distal end of the DOW are accommodated inside the proximal portion of the protective sheath assembly 310. The protective sheath assembly is then inserted into the Y-adaptor 308 with the distal end of the protective sheath assembly 310 passing the hemostasis valve mounted in the Y-adaptor 308. The DOW is then advanced toward the treatment site, followed by removal of the protective sheath assembly 310. The removal of the protective sheath assembly also can be done before the DOW 312 is advanced toward the treatment site. In this way, a balloon catheter with a soft tip can be easily and quickly loaded into a blood vessel through the protective sheath assembly, via introduction through a Y-adaptor and a hemostasis valve.

It should be understood that the embodiments shown are given only for the purpose of illustration and should not be taken as limiting the scope of the present invention. Many modifications can be made by one skilled in the art without departing from the scope and spirit of the present invention.

What is claimed is:

1. A protective sheath assembly that fits over a catheter having a distal end portion to protect the distal end portion of the catheter when introduced into a blood vessel through a blood flow preventing valve, comprising:

a protective sheath having a proximal end, a distal end that covers the distal end portion of the catheter when passing through the blood flow preventing valve, and an elongated body defining a lumen along a longitudinal axis of said protective sheath, said lumen having a proximal portion and a distal portion, wherein the cross-sectional diameter of the distal portion of the lumen is larger than the maximum diameter of the catheter so that said catheter can be moved through the lumen, and wherein at least a portion of the protective sheath remains in the blood flow preventing valve.

2. The protective sheath assembly of claim 1, wherein the distal end portion of the catheter comprises a soft tip.

3. The protective sheath assembly of claim 1, wherein the distal end portion of the catheter comprises a balloon.

4. The protective sheath assembly of claim 1, wherein the distal end portion of the catheter comprises an occlusion device.

5. The protective sheath assembly of claim 1, wherein the distal end portion of the catheter comprises a dilator.

6. The protective sheath assembly of claim 1, wherein the distal end portion of the catheter comprises a filter.

7. A protective sheath assembly for protecting a catheter having a medical device attached to its distal end when the catheter passes through a blood flow preventing valve, comprising:

a protective sheath having a proximal end, a distal end, and an elongated body defining a lumen along a longitudinal axis of said protective sheath, said lumen having a proximal portion and a distal portion, wherein the cross-sectional diameter of the distal portion of the lumen is larger than the maximum diameter of the catheter so that said catheter can be moved through the lumen, and wherein at least a portion of the protective sheath remains in the blood flow preventing valve.

8. The protective sheath assembly of claim 7, wherein the distal end of the catheter comprises a soft tip.

9. The protective sheath assembly of claim 7, wherein the medical device is a balloon.

10. The protective sheath assembly of claim 7, wherein the medical device is an occlusion device.

11. The protective sheath assembly of claim 7, wherein the medical device is a dilator.

12. The protective sheath assembly of claim 7, wherein the medical device is a filter.

* * * * *